United States Patent
Brown et al.

(10) Patent No.: US 6,975,910 B1
(45) Date of Patent: Dec. 13, 2005

(54) MANAGING AN ELECTRONIC COOKBOOK

(75) Inventors: Michael Wayne Brown, Georgetown, TX (US); Kelvin Roderick Lawrence, Round Rock, TX (US); Michael A. Paolini, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/560,386

(22) Filed: Apr. 28, 2000

(51) Int. Cl.⁷ ............................................. G06F 17/30
(52) U.S. Cl. ..................................... 700/90; 707/104.1
(58) Field of Search ... 700/90; 600/407–480; 601/2–4; 351/200–247; 128/915, 916, 920–925; 705/15, 705/26–29; 707/1, 10, 104.1

(56) References Cited

U.S. PATENT DOCUMENTS

| | | | | |
|---|---|---|---|---|
| 4,807,169 A | * | 2/1989 | Overbeck | 708/200 |
| 4,882,724 A | | 11/1989 | Vela et al. | 705/14 |
| 4,992,940 A | | 2/1991 | Dworkin | 705/26 |
| 5,047,614 A | | 9/1991 | Bianco | 235/385 |
| 5,091,713 A | | 2/1992 | Horne et al. | 340/541 |
| 5,412,564 A | * | 5/1995 | Ecer | 600/300 |
| 5,691,684 A | | 11/1997 | Murrah | 235/385 |
| 5,774,871 A | * | 6/1998 | Ferro | 705/15 |
| 5,798,694 A | | 8/1998 | Reber et al. | 340/540 |
| 5,832,446 A | * | 11/1998 | Neuhaus | 705/1 |
| 5,884,281 A | * | 3/1999 | Smith et al. | 705/26 |
| 5,890,128 A | * | 3/1999 | Diaz et al. | 705/2 |
| 5,899,502 A | * | 5/1999 | Del Giorno | 283/67 |
| 5,954,640 A | * | 9/1999 | Szabo | 600/300 |
| 5,960,440 A | * | 9/1999 | Brenner et al. | 707/104.1 |
| 5,969,316 A | * | 10/1999 | Greer et al. | 235/375 |
| 5,969,606 A | | 10/1999 | Reber et al. | 340/540 |
| 5,983,200 A | | 11/1999 | Slotznick | 705/26 |
| 6,023,683 A | | 2/2000 | Johnson et al. | 705/26 |
| 6,123,259 A | * | 9/2000 | Ogasawara | 235/380 |
| 6,204,763 B1 | | 3/2001 | Sone | 340/568.1 |
| 6,236,974 B1 | * | 5/2001 | Kolawa et al. | 705/7 |
| 6,246,998 B1 | * | 6/2001 | Matsumori | 705/27 |
| 6,301,564 B1 | * | 10/2001 | Halverson | 705/15 |
| 6,341,271 B1 | | 1/2002 | Salvo et al. | 705/28 |
| 6,370,513 B1 | * | 4/2002 | Kolawa et al. | 705/10 |
| 6,381,614 B1 | * | 4/2002 | Barnett et al. | 707/104.1 |
| 6,418,416 B1 | | 7/2002 | Rosenberg et al. | 705/28 |
| 6,430,541 B1 | | 8/2002 | Brown et al. | 705/28 |
| 6,513,017 B1 | * | 1/2003 | Howard et al. | 705/28 |
| 6,553,386 B1 | * | 4/2003 | Alabaster | 707/104.1 |
| 2001/0025279 A1 | * | 9/2001 | Krulak et al. | 707/3 |
| 2002/0026363 A1 | * | 2/2002 | Dunaway, Jr. | 705/15 |
| 2002/0042745 A1 | * | 4/2002 | Nacey | 705/15 |

\* cited by examiner

FOREIGN PATENT DOCUMENTS

JP      11-066170 A    *   3/1999

*Primary Examiner*—Maria N. Von Buhr
(74) *Attorney, Agent, or Firm*—Marilyn Smith Dawkins; Dillon & Yudell LLP

(57) ABSTRACT

According to the present invention, dietary needs designated for a particular user are received in a common transmittable data format at a data processing system associated with a particular home base, wherein the data processing system has access to multiple electronic recipes. The dietary needs designated for the particular user are compared with a selection of electronic recipes that are preparable at the particular home base from among the multiple accessible electronic recipes. At least one meal plan is designated from among the selection of electronic recipes that satisfies the dietary needs of the particular user, such that an electronic meal plan is specified on said data processing system for preparation at a particular home base according to dietary needs of a particular user.

91 Claims, 7 Drawing Sheets

MANAGING AN ELECTRONIC COOKBOOK

BACKGROUND OF THE INVENTION

1. Technical Field

The present invention relates in general to an electronic cookbook and in particular to a method, system and program for managing an electronic cookbook. Still more particularly, the present invention relates to a method, system and program for managing an electronic cookbook to meet the dietary needs of multiple diverse users.

2. Description of the Related Art

As the tide is turning towards a paperless world, computers are becoming more prevalent in order to replace many functions previously performed utilizing paper. In particular, computing devices, such as personal digital assistants, laptop computers and cellular/digital telephones are becoming more commonplace as a personal, portable computer system. Such devices are typically designed to provide reliable and efficient transmittal and storage of data. For example, many digital telephones not only include capabilities to transmit and receive voice data, but to transmit and receive electronic data such as stock quotes, current weather and news. A small display device is typically provided to display the electronic data.

In the cooking world, multiple types of recipes and meal plans have been moved into an electronic format. For example, a user can purchase an electronic cookbook device with a kitchen friendly output monitor that contains multiple searchable recipes and can be updated with new recipes. In addition, meal plans for specific types of events, such as a Halloween party may be included. Some electronic cookbook devices further include functions for filtering recipes according to criteria entered by the user such as calories/serving, fat/serving and particular ingredients.

In addition to electronic cookbook devices, the Internet provides access to multiple diverse web sites comprising hundreds and thousands of electronic recipes. Typically, a user can search the electronic recipes at each web site according to criteria such as ingredients, type of cuisine, etc. In addition, a user may search web sites according to meal plans available at the web site. For example, the web site cooking.com provides multiple searchable recipes and designated meal plans that are accessible to any user.

However, current electronic recipes and cookbooks accessed either through a device or through the Internet are limited. It would be advantageous to utilize an electronic cookbook that is enabled to learn dietary needs of typical occupants, learn the dietary needs of visitors, and manage recipe selections accordingly. In learning typical occupants and visitors dietary needs, electronic recipes and meal plans accessible to the electronic cookbook from multiple sources are preferably automatically filtered according to the dietary needs. In addition to filtering electronic recipes and meal plans based on dietary needs, the electronic cookbook preferably has access to data such as the current environment, food already consumed by occupants and visitors that day or week, exercise performed by occupants and visitors that day or week, current medication usage for the occupants and visitors and other food and health related data that may be utilized to filter electronic recipes and meal plans for typical occupants and/or visitors. Moreover, the food and kitchen supplies available for the user in preparing meals are preferably utilized by the electronic cookbook to filter electronic recipes and meal plans for preparation in a particular kitchen.

SUMMARY OF THE INVENTION

In view of the foregoing, it is therefore an object of the present invention to provide an improved electronic cookbook.

It is another object of the present invention to provide an improved method, system and program for managing an electronic cookbook.

It is yet another object of the present invention to provide an improved method, system and program for managing an electronic cookbook to meet the dietary needs of multiple diverse users.

According to the present invention, dietary needs designated for a particular user are received in a common transmittable data format at a data processing system associated with a particular home base, wherein the data processing system has access to multiple electronic recipes. The dietary needs designated for the particular user are compared with a selection of electronic recipes that are preparable at the particular home base from among the multiple accessible electronic recipes. At least one meal plan is designated from among the selection of electronic recipes that satisfies the dietary needs of the particular user, such that an electronic meal plan is specified on said data processing system for preparation at a particular home base according to dietary needs of a particular user.

All objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF ILLUSTRATIVE EMBODIMENT

The present invention may be executed in a variety of systems, including a variety of computing systems and electronic devices under a number of different operating systems. In a preferred embodiment of the present invention, the computer system is a portable computing system such as a notebook computer, a palmtop computer, a personal digital assistant, a telephone or other electronic computing system that may also incorporate communications features that provides for telephony, enhanced telephony, messaging and information services. However, the computer system may also be, for example, a desktop computer, a network computer, a midrange computer or a mainframe computer. Preferably, in order to enable at least one of these communications features, the computer system is able to be connected to a network, such as the Internet by either a wired link or wireless link. In addition, the computer system may be a stand-alone system or part of a network such as a local-area network (LAN) or a wide-area network (WAN). Therefore, in general, the present invention is preferably executed in a computer system that performs computing tasks such as manipulating data in storage that is accessible to the computer system. In addition, the computer system includes at least one output device and at least one input device.

Figure 1:
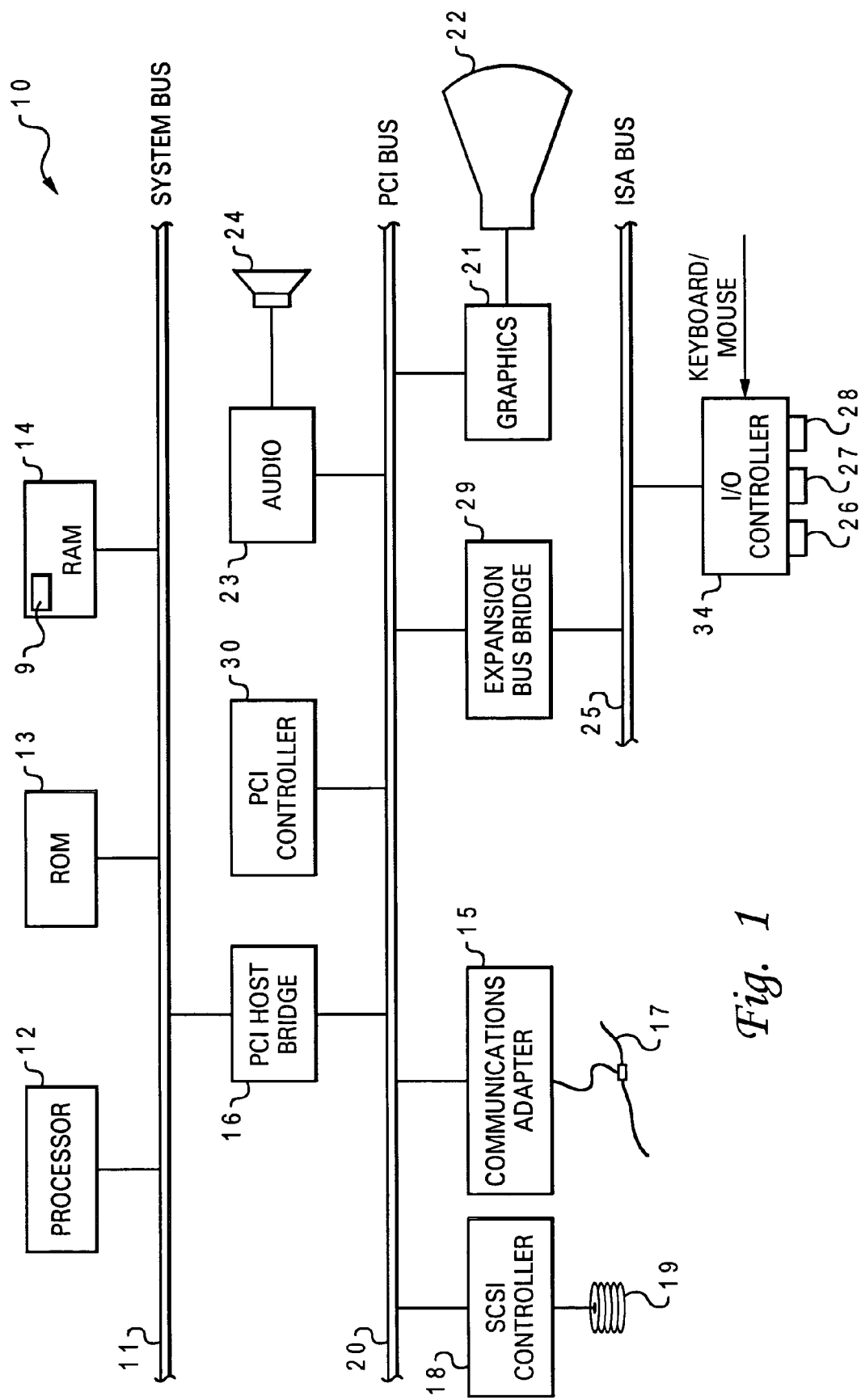
FIG. 1 depicts a block diagram of a typical computer system that may utilize a preferred embodiment of the present invention.

Referring now to the drawings and in particular to FIG. 1, there is depicted a block diagram of one embodiment of a computer system that may utilize the present invention. As depicted, data processing system 10 includes at least one processor 12, which is coupled to system bus 11. Each processor 12 is a general-purpose processor, such as IBM's PowerPC™ processor that, during normal operation, processes data under the control of operating system and application software stored in random access memory (RAM) 14 and Read Only Memory (ROM) 13. The operating system preferably provides a graphical user interface (GUI) to the user. Application software contains instructions that when executed on processor 12 carry out the operations depicted in the flowcharts of FIGS. 5, 6, 7 and others described herein.

Processors 12 are coupled via system bus 11 and Peripheral Component Interconnect (PCI) host bridge 16 to PCI local bus 20. PCI host bridge 16 provides a low latency path through which processor 12 may directly access PCI devices mapped anywhere within bus memory and/or I/O address spaces. PCI host bridge 16 also provides a high bandwidth path for allowing PCI devices to directly access RAM 14.

PCI local bus 20 interconnects a number of devices for communication under the control of PCI controller 30. These devices include a Small Computer System Interface (SCSI) controller 18, which provides an interface to SCSI hard disk 19, and communications adapter(s) 15, which interface data processing system 10 to at least one data communication network 17 comprising wired and/or wireless network communications. In addition, an audio adapter 23 is attached to PCI local bus 20 for controlling audio output through speaker 24. A graphics adapter 21 is also attached to PCI local bus 20 for controlling visual output through display monitor 22. In alternate embodiments of the present invention, additional peripheral components may be added. For example, in alternate embodiments, a tactile display component may be provided.

PCI local bus 20 is further coupled to an Industry Standard Architecture (ISA) bus 25 by an expansion bus bridge 29. As shown, ISA bus 25 has an attached I/O (Input/Output) controller 34 that interfaces data processing system 10 to peripheral input devices such as a keyboard and mouse (not illustrated) and supports external communication via parallel, serial and universal serial bus (USB) ports 26, 27, and 28, respectively.

Figure 2:
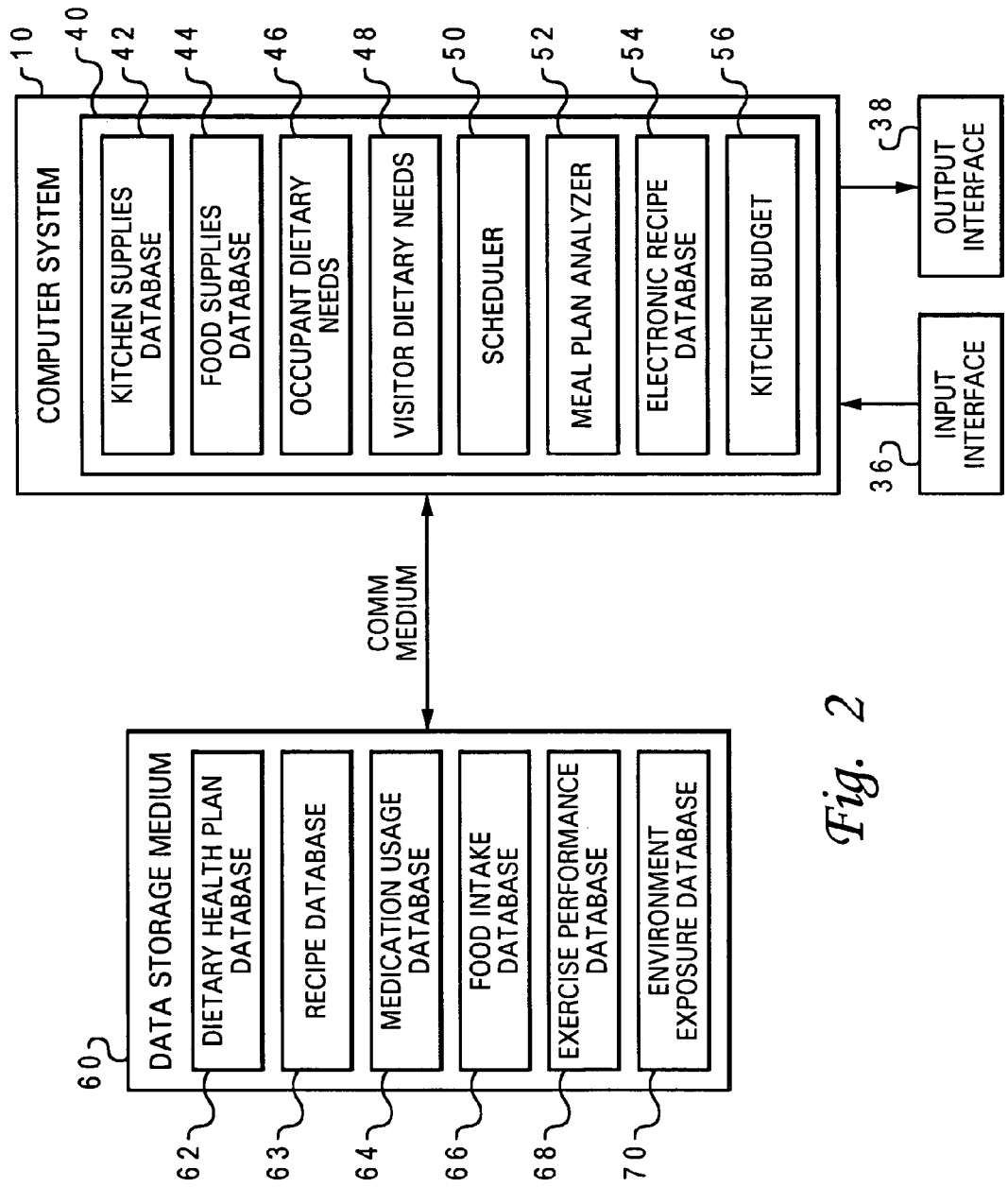
FIG. 2 illustrates a block diagram of an electronic cookbook system in accordance with the method, system and program of the present invention.

With reference now to FIG. 2, there is illustrated a block diagram of an electronic cookbook system in accordance with the method, system and program of the present invention. As depicted, computer system 10 receives data from a data storage medium 60 via a communications medium(or across a communication interface). The communications medium may comprise wired or wireless communications or other communications media that enables transmission of data. Moreover, the communications medium may comprise a link to a network, such as the Internet, or a straight data link. Furthermore, data may be transmitted from data storage medium 60 to an electronic mail address that is accessible to computer system 10.

Data exchange across the communications medium is advantageously performed in at least one of multiple available data transmission protocols and is preferably supported by a common data structure format, such as the extensible mark-up language (XML) data structure format. Data transmission protocols may include, but are not limited to, Transmission Control Protocol (TCP), Internet Protocol (IP), Hypertext Transfer Protocol (HTTP), and Bluetooth. In addition, data may be transmitted in a secure manner via encryption or by technologies, such as secure socket layer (SSL) or virtual private networks (VPN).

An example of an XML data file, as depicted below, preferably contains data that is distinguished by attributes on elements and may be wrappered within a larger element. The XML data file is intended as an example of elements and data that could be included in an XML data file transmitted from data storage medium 60 to computer system 10. For example, the data attributed to element "<TimeStamp></TimeStamp>" designates the time in seconds since the Epoch, 00:00:00 Jan. 1, 1970 UTC that the dietary and health related data was started recording. The time range indicates the range of time between which the data is valid.

<USER HEALTH TimeStamp="888965153" TimeStamp= "888965153" TimeRange="888965153, 888968000" UserID= "BorisB" Age="14" CalorieAllowance="2500/day" FatAllowance="50/day" ProteinRequirement="40/day" Event= "soccer game" EventTime="2.25.2003" Recipe="tuna.doc" Recipe="chocolatepie.doc" Medication="zapalac23" Dosage="2/day" Intake="32 oz. water" Intake= "cheeseburger,400 cal,30 g fat" Fitness="600 cal" TempExposure="60, 70"

A second example of the same data in an alternate XML data format that includes elements is illustrated below.

<TimeStamp>888965153</TimeStamp>
    <TimeRange>888965153,888968000</TimeRange>
    <UserID>BorisB</UserID>
    <Age>14</Age>
    <CalorieAllowance>2500/day</CalorieAllowance>
    <FatAllowance>50/day</FatAllowance>
    <ProteinRequirement>40/day</ProteinRequirement>
    <Event>soccer game</Event>
    <EventTime>2.25.2003</Event>
    <Recipe>tuna.doc</Recipe>
    <Recipe>chocolatepie.doc</Recipe>
    <Medication>zapalac23</Medication>
    <Dosage>2/day</Dosage>
    <Intake>32 oz. water</Intake>

```
<Intake>cheeseburger,400 cal,30 g fat</Intake>
<Fitness>600 cal</Fitness>
<TempExposure>60,70</TempExposure>
```

In the examples, dietary and health related data for a user "BorisB" is transmittable in the XML data format. For example, the user's dietary health plans include a calorie allowance of 2500 calories per day, a fat allowance of 50 grams per day, a protein requirement of 40 grams per day and an upcoming soccer game. In addition, recipes included with the user's dietary and health related data include a tuna recipe and a chocolate pie recipe that are transmitted as documents that are advantageously in the XML data format. The recipe for tuna, for example, may be acquired by the user at a friend's house. The user is taking a medication "zapalac23" twice a day and has taken in 32 oz. water and a cheeseburger with 400 calories and 30 g of fat during the time range. In addition, the user has burned 600 calories in exercise and has been exposed to temperatures ranging between 60° and 70° F.

In the example of the XML data format as the common transmittable data structure format, a data validation file such as a document type definition (DTD) or schema is preferably utilized to validate XML data files. In addition, a schema preferably translates multiple XML data files. Moreover, a style sheet such as an extensible style sheet language (XSL) file is preferably utilized to provide a style specification for the XML data at the receiving system. In particular, DTDs, schemas, and XSL files may be, for example, transmitted with an XML data file to a receiving system or downloaded at the receiving system from an alternate source.

Data storage medium 60 preferably comprises dietary and health related data that is specified for a particular user or users. In the present example, the dietary and health related data stored in data storage medium 60 includes dietary health plans database 62, medication usage database 64, a food intake database 66, an exercise performance database 68 and an environment exposure database 70. The databases are preferably data storage structures that hold multiple entries and may be searched and/or filtered according to particular criteria and are easily converted to a common transmittable data format. In addition, as will be understood by one with ordinary skill in the art, multiple types of security methods and filters may be applied to the data stored in data storage medium 60 to restrict access thereto. Moreover, in alternate embodiments, alternate types of data may be stored in data storage medium 60. In addition, in alternate embodiments, the data stored in data storage medium may be combined into a single data storage structure.

Dietary health plans database 62 preferably includes a profile of a user that is specified to the dietary needs of that user. For example, dietary needs of a user may include a dietary health plan that specifies daily food allowances qualified according to categories including, but not limited to, serving size, calories, fat, carbohydrates, sodium, cholesterol, protein. However, the dietary needs of a user are not necessarily limited to dietary elements such as protein. Dietary needs may also provide for extra and/or preferred dietary items, such as sugar, alcohol, etc.

In addition, dietary needs may indicate particular food allergies, food preferences, preferred substitutions, and preferred preparation techniques. Moreover, dietary needs may indicate a person's upcoming scheduling events that are effected by dietary intake or include dietary intake. For example, dietary needs may indicate that a user will participate in a marathon or other athletic event in two weeks. Alternatively, dietary needs may indicate that a user will attend three holiday parties in the next week. Moreover, dietary needs may indicate that a user will be traveling to a different climate in the next week.

Moreover, dietary needs as prescribed by a physician or other health specialist may be included in dietary health plans database 62. Additional personal data such as the user's height, weight, sex, and other personal data may also be included.

Recipe database 63 advantageously includes multiple recipes that have been retrieved by a user. For example, a user may request a particular recipe when dining at a friend's house and the recipe is retrieved from the friend's electronic cookbook into recipe database 63 of data storage medium 60. In another example, a user may download recipes from a web site into recipes database 63. Moreover, in ordering from an electronic menu at a restaurant, as described in U.S. Pat. No. 6,618,062, herein incorporated by reference, a user may receive recipes for food items ordered from the restaurant at recipe database 63. For example, an individual may order a chocolate pie at a restaurant and receive a transmission from the restaurant server to data storage medium 60 that includes a recipe for the chocolate pie.

Medication usage database 64 advantageously includes a list of each medication being taken by a user or users. In addition, a medication summary provided by the manufacturer that includes data such as a schedule for taking medication, possible side effects and food/drug conflicts, is preferably included. Medication usage may include prescription medications, over-the-counter medications and vitals or nutritional supplements. Medication usage database 64 may be determined, for example, by the method, system and program disclosed in U.S. patent application Ser. No. 09/560,392, herein incorporated by reference.

Food intake database 66 preferably includes a recording of each food item consumed by a user over a period of time. In addition, a dietary breakdown of each food item that includes the serving size, ingredients and dietary facts is preferably included. Food intake may include multiple types of consumable items, including drinks. Food intake database 66 may be determined, for example, by the method system and program disclosed in U.S. Pat. No. 6,618,062, herein incorporated by reference, where the food is ordered and purchased from a particular food service or restaurant venue. In addition, food intake database 66 may be determined, for example, by the method, system and program for the present invention, where the food is prepared in a particular home base accord to a meal plan determined by an electronic cookbook.

Exercise performance database 68 advantageously includes a recording of fitness activity for a user or users. In addition, cumulative fitness activity for a user or users over a specific period of time is preferably included in exercise performance database 68. Fitness activity may include, for example, exercise directed and measured by an exercise machine and exercise performed independent of an exercise machine. Exercise performance database 68 may be determined, for example, by the method system and program disclosed in U.S. Pat. No. 6,746,371, U.S. patent application Ser. No. 09/561,130, now abandoned, and/or U.S. Pat. No. 6,601,016, each herein incorporated by reference.

Environment exposure database 70 preferably includes a recording of the environment exposure of a user or users over a period of time. Environment exposure may include indicators such as temperature, humidity, air purity, wind levels and other environment indicators. Environment exposure may be recorded for both indoor and outdoor environments. Environment exposure database 70 may be determined, for example, by the method, system and program disclosed in a U.S. Pat. No. 6,604,023, U.S. Pat. No. 6,622,115, and/or U.S. Pat. No. 6,636,808, each herein incorporated by reference.

Computer system 10 preferably accesses a data storage medium 40 that includes, but is not limited to including, a kitchen supplies database 42, a food supplies database 44, an occupants dietary needs database 46, a visitor dietary needs database 48, a scheduler 50, a meal plan analyzer 52, a recipes database 54, and a kitchen budget 56. In the present embodiment, data storage medium 40 is accessible locally to computer system 10, however in alternate embodiments data storage medium 40 may be externally or remotely accessible to computer system 10, such as via a network connection to a universally accessible database, as will be further described.

Computer system may receive health and dietary related data from multiple diverse sources, including data storage medium 60, input interface 36 and other data processing systems(not shown). Input interface 36 may comprise, but is not limited to, a keyboard, a mouse, a stylus, and a vocal recognition system.

Computer system 10 is preferably associated with a particular home base or personal kitchen associated with a residence. A residence may include one occupant or multiple occupants. In addition, a residence may include multiple expected and unexpected visitors. Advantageously, the primary person (primary chef) who prepares meals at the residence is provided with computer system 10 which functions to manage an electronic cookbook, executable on computer system 10, according to the dietary health plans for the typical occupants and visitors at the residence. In addition, as will be further described, computer system 10 functions to manage the electronic cookbook according to multiple factors including, but not limited to, scheduling, environment exposure, prescription usage, previous food intake, cumulative fitness activity, and other user designated factors.

In addition, computer system 10 may be associated with more than one home base, and is advantageously portable to the multiple home bases. For example, a personal chef may prepare and cook meals at multiple residences. For each residence, computer system 10 functions to manage an electronic cookbook that is specified according to the dietary health plans and other factors of the occupants and visitors of each residence.

Dietary and health related data received at computer system 10 is preferably stored according to the type of user or users. For example, if the dietary and health related data is from a user that is an occupant of the residence associated with computer system 10, the dietary and health related data is stored in occupant dietary needs 46. However, if the dietary and health related data is from a user that is a visitor of the residence associated with computer system 10, the dietary and health related data is stored in visitor dietary needs 48. Occupants and visitor are preferable distinguished for multiple functions by the primary user of computer system 10. For example, visitor dietary needs may be given priority over occupants. In another example, a typical number of servings may be planned for each meal for the designated occupants of a home and adjusted according to visitors.

Kitchen supplies database 42 preferably includes a recording of the kitchen supplies available in a kitchen of a particular residence. Kitchen supplies may include, but are not limited to including, appliances, dishware, silverware, cookware, cooking utensils and bakeware. In addition, a food supplies database 44 preferably includes a recording of the food supplies available in a kitchen of a particular residence. Food supplies may include store-bout food items and home-grown food items. Bot kitchen supplies database 42 and food supplies database 44 may be monitored by an electronic storage management system described in U.S. patent application Ser. No. 09/560,320, herein incorporated by reference.

Scheduler 50 includes multiple diverse events. First, scheduler 50 preferably includes scheduling events for the residence, such as any parties that are planned, expected visitors, designated meal times, etc. In addition, scheduler 50 advantageously includes scheduling events for the primary chef for the home base, such as preparation and cook time availability, expected parties and functions to attend, an exercise schedule, a medication intake schedule, etc. Moreover, scheduler 50 preferably includes scheduling events for the occupants of the residence and any relevant scheduling events for visitors to the residence.

In addition scheduler 50 may include a predetermined meal plan and scheduling of when particular ingredients need to be purchased, prepared and cooked for the meal plan. For example, if a meal plan on Sunday includes fish, scheduler 50 may include a reminder to purchase the fish that day. In particular, scheduler 50 is enabled to transmit a list of all necessary food and kitchen supplies to the electronic storage management system that compares the necessary supplies with current inventory to determine necessary inventory purchases. The necessary inventory purchases are advantageously searched for among multiple on-line retailers in order to determine a recommended electronic shopping list for making purchases from at least one on-line retailer as described in U.S. Pat. No. 6,430,541, herein incorporated by reference.

In another example, if a Monday dinner includes chicken that is currently frozen, a reminder to take the chicken out to thaw that morning may be included as a scheduled event. In addition, a schedule event may be utilized to determine a control signal for defrosting the chicken by a freezer that is controlled according to planned cooking events as determined by the method, system and program described in U.S. patent application Ser. No. 09/560,320, herein incorporated by reference.

In yet another example, if a party is planned for Friday night, a schedule of appetizers that can be prepared a few days in advance may be added to scheduler 50 in order to reduce preparation on the day of the event.

Moreover, scheduler 50 preferably includes data indicating when particular food items are in season or available. For example, the months that oysters are in season may be indicated in scheduler 50. In addition, computer system 10 can preferably access server systems that provide downloadable food related scheduling events that can be added to scheduler 50. For example, computer system 10 may access the weekly sales and electronic coupons from a local grocery from a server system. Thereby, scheduler 50 would include schedule events that designate particular products that will be available on sale or purchase with a coupon discount that week.

Furthermore, scheduler 50 preferably stores meals plans as prepared at a particular home base. Thereby, meal plans can be replicated on other days. In addition, previously prepared meals and other food items can be referred back to with any notes that the user recorded with the meal plan and recipes. Moreover, meals prepared according to guests may be referred back to. For example, meals prepared when guest A was eating at the residence may be recorded. A particular recipe that was enjoyed by guest A may be noted. In addition, a particular recipe that was not enjoyed by guest A may also be noted.

Kitchen budget 56 for a particular residence preferably includes budget amounts for kitchen supplies and food per year, month or week and may also include division for budgeting for upcoming events and parties. Individual budget amounts within kitchen budget 56 may be set by the user, or may be determined by computer system 10 based on previous spending and current budget constraints. In addition, scheduled events in scheduler 50 may be referenced in determining kitchen budget 56. For example, if a user spent $400 on a thanksgiving dinner the year before, $400 is preferably added to the thanksgiving dinner portion of kitchen budget 56 for the following year. However, if ten additional relatives are expected for the next thanksgiving, the thanksgiving dinner amount may be increased to adjust for the additional visitors. Alternatively, if a user's total available budget decreases, the thanksgiving dinner amount may be decreased.

Recipe database 54 preferably includes multiple diverse electronic recipes. Electronic recipes may include a dietary description of the contents of the recipe such as serving size, calories, fat, sodium, carbohydrates, protein and vitamin content. In addition recipe database 54 may include instructions on cooking techniques, substitutions, alternative ingredients, measurement conversions and other data that is typically provided in a cookbook. Recipe database 54 may be supplemented via user input to input interface 36, via electronic recipes transmitted from data storage medium 60, and via a network connection to a network server from which recipes are accessible.

Electronic recipes included in recipe database 54 can preferably be categorized by the user according to multiple diverse criteria. For example, a user may designate particular recipes in a "family favorites" category. In addition, other recipes may be designated by event, such as Thanksgiving, Christmas, or a birthday. Moreover, recipes may be designated according to visitor preferences. In addition to categorizing recipes, the electronic recipes are preferably adjustable according to a cook's preferences and may include notes added by a cook. For example, a cook may substitute a particular ingredient and decide to change the recipe to the substitution. In addition, a cook may substitute a particular ingredient that causes the food to turn out poorly. The cook may add a note to the recipe to remind themself and others about the results of the substitution.

Meal plan analyzer 52 preferably compares dietary health needs of those for whom a meal will be prepared with recipes database 54. As previously described, health and dietary related data for a particular user are preferably transmitted to computer system 10 via a communications medium. Health and dietary related data preferably includes at least a dietary health plan for the user and may also include medication usage, food intake, exercise performance, and/or environment exposure. Meal plan analyzer 52 utilizes the health and dietary related data to filter electronic recipes database 54 in order to provide a selection of meal plans that include electronic recipes that are acceptable in view of the user's health and dietary related data.

In addition, as described, health and dietary related data received for a user is stored in either occupant dietary needs database 46 or visitor dietary needs database 48. Meal plan analyzer 52 is preferably enabled to filter electronic recipes database 54 utilizing multiple previously stored user dietary needs from occupant dietary needs database 46 and visitor dietary needs database 48. A person planning a meal or meals is preferably enabled to designate which occupant and visitor dietary needs should be utilized when filtering electronic recipes database 54.

In comparing dietary health needs with recipes database 54, meal plans of selections of recipes are preferably compiled. For example, if the dietary health needs of multiple users include planning a meal with a meat serving, a vegetable serving, a fruit serving and a light dessert, meal plans consisting of meat serving options, vegetable serving options, fruit serving options and light dessert serving options may be designated. The dietary health needs of the occupants and visitors for a particular meal or meals may differ widely. For example, if a vegetarian and a meat-lover may dine together at a residence. In such a case, a meal plan that includes vegetarian specific recipe selections may be adapted to include meat. Alternatively, a meal plan that includes meat specific recipes may be adapted for a vegetarian.

As previously described, dietary health needs for a user advantageously include scheduling events for the user, including upcoming athletic events and travel. In particular, in comparing dietary health needs with recipes database 54, meal plans of selections of recipes that compensate for upcoming events are preferably compiled. For example, if a user has a soccer game in two days, then the night before the soccer game recipes that are preferable for "carbo-loading" may be designated. In addition, special jet lag diets may be selected if a user plans to fly across multiple time zones.

In addition, in comparing dietary health needs with recipes database 54, recipes that include known food and drug conflicts with current medication for a user are preferably filtered out. Moreover, previous meals are preferably taken into consideration and utilized when filtering recipes database 54. For example, if a first occupant had a hamburger for lunch and a second occupant had pasta for lunch, meal plans for dinner including hamburgers or pasta are preferably not provided. Furthermore, current physical fitness is preferably taken into consideration and utilized when filtering recipes database 54. For example, for a person that has been sedentary that day, but is usually very active, meal plans that include reduced calorie foods may be provided. Moreover, environment exposure is preferably taken into consideration and utilized when filtering recipes database 54. For example, if the current weather is frigid cold and the occupants are significantly exposed to the cold, meal plans that include warm and hearty dishes may be included. Alternatively, in a hot, humid climate, meal plans may include cool dishes that supplement sodium and liquids.

Meal plan analyzer 52 preferably also compares schedule events in scheduler 50 with electronic recipes database 54 to designate electronic recipes that meet the schedule events criteria. For example, if the person cooking the meal has 1 hour to prepare and cook the meal, then meal plans with recipes that will only take 1 hour to prepare and cook will be designated. In addition, if scheduler 50 indicates that two of the occupants eating a dinner meal will eat at six and another three will eat at nine, meal plan analyzer 52 preferably filters electronic recipe database 54 and selects meal plans of recipes that are easily storable and re-heatable.

Meal plan analyzer 52 preferably also compares available kitchen supplies and food supplies from kitchen supplies database 42 and food supplies database 44 with electronic recipes database 54 in order to designate electronic recipes for which kitchen and food supplies are available. In filtering the recipes database 54 with the kitchen and food supplies, meal plan analyzer 52 may provide for substitutions and alternate products such that the available kitchen and food supplies may be utilized with recipes that previously included kitchen and food supplies not readily available in the kitchen. In addition, meal plan analyzer 52 preferably filters recipes database 54 with kitchen and food supplies according to the number of servings that are expected. Therefore, if food supplies to produce two servings of a recipe are available, but six servings are needed, an indicator of what additional ingredients need to be purchased for the recipe may be supplied.

Meal plan analyzer 52 preferably also compares available budget constraints in kitchen budget 56 with electronic recipes database 54 in order to designate meal plans meal can be made within the available budget constraints. For example, if a family of four has budgeted $20 for three days of dinners, meal plans which include recipes that utilize low priced ingredients and result in a large amount of servings would be designated. In addition, if a significant number of recipes could be made by the user and would meet budget constraints if the kitchen included a large stock pot and kitchen budget 56 includes resources for purchasing that stock pot, meal plan analyzer 52 might suggest purchasing the stock pot and show examples of meal plans that utilize the stock pot. Meal plan analyzer 52 may further access multiple web pages that provide stock pots for purchase, retrieve the prices provided on the web page and make recommendations for on-line ordering. Moreover, the stock pot may be added to an electronic shopping manager or consumer preference manager, as described in U.S. patent application Ser. No. 9/560,320 and U.S. patent application Ser. No. 09/560,392, each herein incorporated by reference, such that the user is notified within a particular proximity of a store that provides a stock pot within the budgeting constraints of the user.

Results of analysis performed by meal plan analyzer 52 are preferably output to the user via output interface 38 according to output preferences set by the user. Examples of output interfaces include, but are not limited to, a graphical display, an electronic paper, an audio speaker, audio headphones, a tactile detectable device, or a printer. In particular, the user may select and provide the type of output device and may upgrade the type of output device as technology advances. The output preferences may include, but are not limited to, specifications such as the size, type and coloring of a font in a graphical display, the type of tactile-detectable output (e.g. Braille), the language or the metric amount displayed.

A user preferably makes a selection from among the meal plans provided as a result of meal plan analyzer 52. The output of the selections of recipes is preferably adjustable by the user. For example, the user may select to view the selection of recipes according to order of preparation. In another example, the user may select to view the ingredients and amounts of the selection of recipes. In another example, the user may select to view only the titles of the selection of recipes such that additional graphics or other presentation enhancements may be selected and a meal menu printed. Moreover, a user may select to view the recipes in a print preview. In addition, a user may select to view additional instructions regarding cooking techniques utilized in preparing the recipes.

In many embodiments, computer system 10 is advantageously a portable data processing system such as personal digital assistant, laptop computer or other pervasive computing device that is easily transportable. In addition, computer system 10 is advantageously customizable to a user's preferences. For example, a user may provide computer system 10 with a black and white display while another user may provide a color display.

Figure 3:
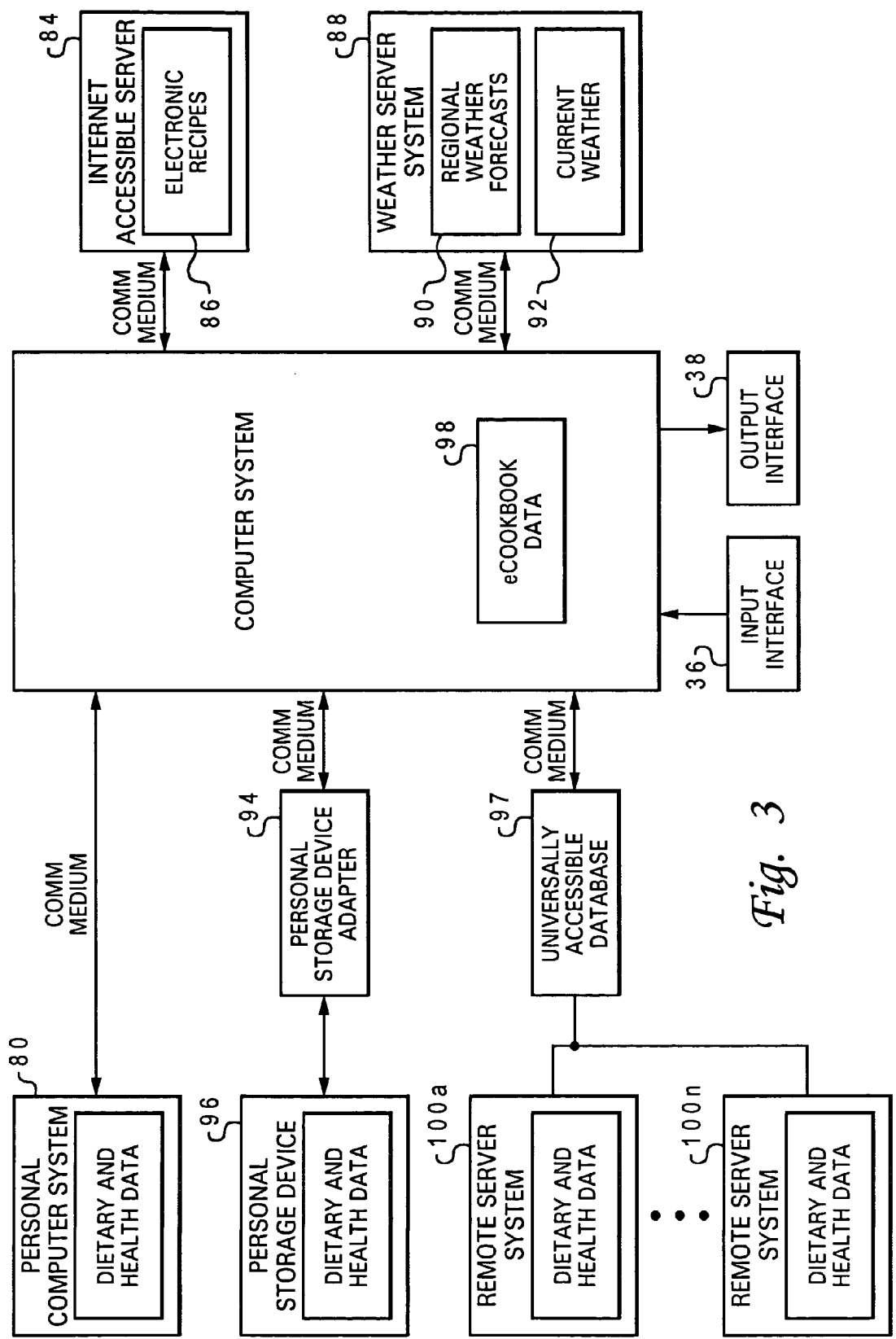
FIG. 3 depicts a first embodiment of a block diagram of a system for updating and accessing an electronic cookbook in accordance with the method, system and program of the present invention.

Referring now to FIG. 3, there is depicted a first embodiment of block diagram of a system for updating and accessing an electronic cookbook in accordance with the method, system and program of the present invention. As illustrated, a computer system 10 comprises the electronic cookbook (eCookbook) data such as the kitchen supplies database, food supplies database, occupant dietary needs, visitor dietary needs, scheduler, meal plan analyzer, recipes and kitchen budget depicted in FIG. 2 of the present invention. The dietary and health data from multiple users may be accessed at computer system 10 via multiple data storage media.

In one example, the dietary and health data for users may be accessed from personal computer system 80 at computer system 10. Personal computer system 80 preferably communicates with computer system 10 via a communications medium which as previously described, may comprise a wired or wireless medium and may utilize a network or a straight data link. A common transmittable data format, such as XML is preferably utilized to support data transmission across the communication medium.

In another example, the dietary and health data for users may be accessed from a personal storage device 94 proffered by the user. A personal storage device adapter 94 is coupled to computer system 10 via a communications medium to detect personal storage device 94 when within a particular proximity. Personal storage device 94 may include multiple types of transportable data storage mediums, such as smart cards.

In yet another example, the dietary and health data for users is accessed via a universally accessible database 97 that controls access to one of multiple remote server systems 100a–100n according to a universal identifier for a particular user. Universally accessible database 97 preferably includes a database of universal identifiers that each respectively associated with one of multiple remote server systems 100a–100n that are accessible via a network. Universal identifiers may include addresses for web sites and other alphanumeric identifiers that may also require a password for access. Remote server systems 100a–100n may include home computers, network servers, data storage provider servers, and other data processing systems that include data storage mediums for storing dietary and health related data according to a particular universal identifier. A user may access dietary and health related data for that user by entering a universal identifier associated with the user at computer system 10, wherein computer system 10 transmits the universal identifier and a request for the dietary and health related data to universally accessible database 97.

In addition, in the example, computer system 10 may access alternate servers that comprise accessible data for updating eCookbook data 98 via a communications medium. For example, Internet accessible server 84 provides access to electronic recipes 86 that may be selected to update the electronic recipes stored in eCookbook data 98 and or searched from eCookbook 98. In another example, computer system 10 may access weather server system 88 that includes regional weather forecasts data 90 and current weather data 92. As previously described, the current weather conditions may be utilized by the meal plan analyzer of computer system 10 to filter the available electronic recipes. In particular, any of the data included in eCookbook data 98 is preferably undatable via a communication medium with the Internet or other type of network accessible server. Other examples of data accessible via a network accessible server may include, but are not limited to, on-line kitchen supplies and food supplies for purchase, scheduling data, an updated meal plan analyzer application and dietary health plans.

Figure 4:
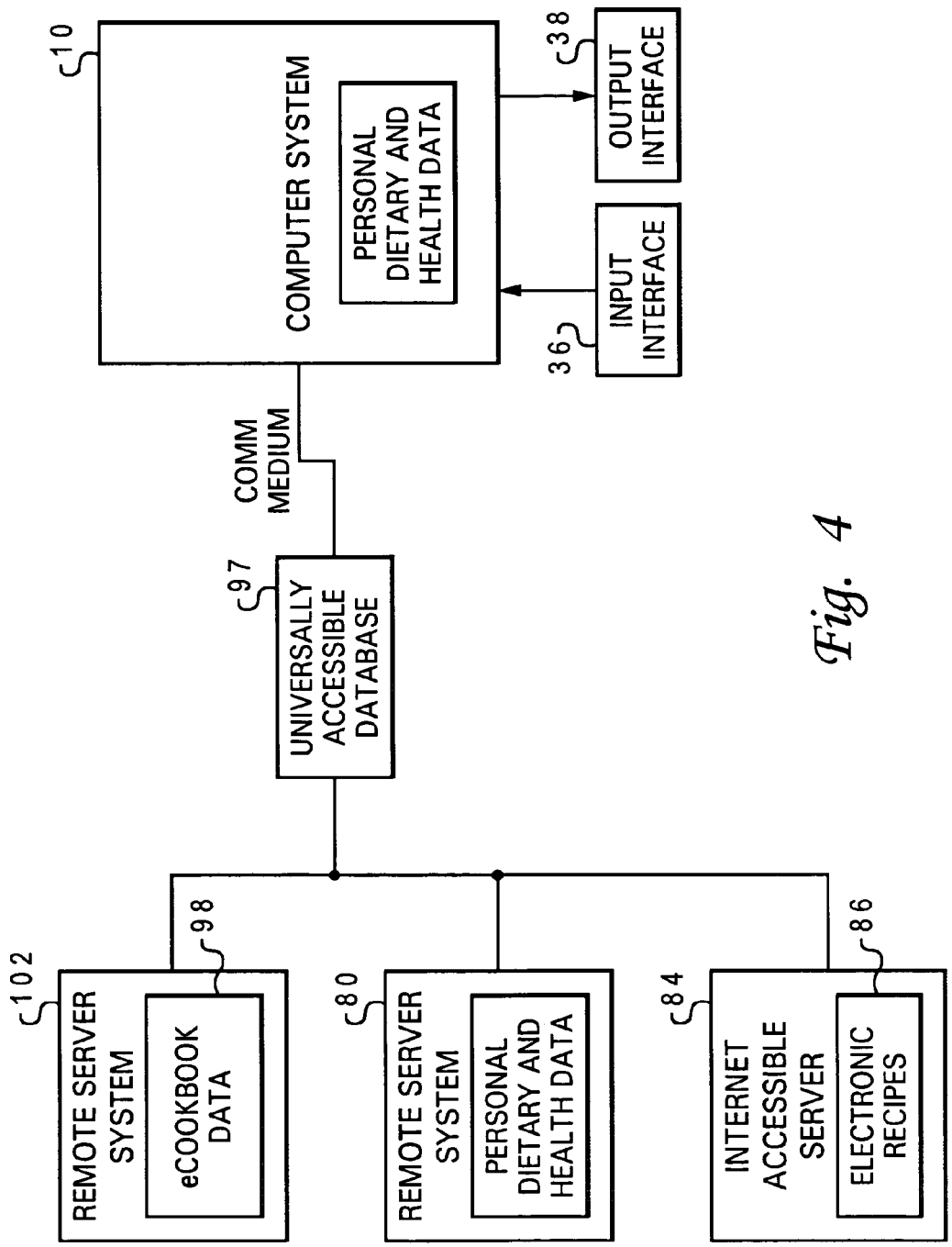
FIG. 4 illustrates a second embodiment of a block diagram of a system for updating and accessing an electronic cookbook in accordance with the method, system and program of the present invention

With reference now to FIG. 4, there is depicted a second embodiment of a block diagram of a system for updating and accessing an electronic cookbook in accordance with the method, system and program of the present invention. As depicted, computer system 10 is a dumb terminal through which universal identifiers and other data may be input via input interface 36 and through which data received from a universally accessible database is output via output interface 38. Personal dietary and health data for a particular user or multiple diverse user may be received at computer system 10 from an alternate personal computer system, a personal storage device or other data storage medium that is accessible to computer system 10.

In the example, computer system 10 accesses universally accessible database 97 via a network communication medium according to a particular universal identifier. Universally accessible database 97 directs access to a remote server system 102 that comprises eCookbook data 98 according to the particular universal identifier. Processing power for analyzing recipes and determining meals plans utilizing eCookbook data 98 is preferably provided by remote server system 102. The designated meal plans are preferably transmittable to computer system 10 for output via output interface 38.

In addition, universally accessible database 97 directs access to Internet accessible server 84 that comprises multiple electronic recipes 86 stored according to a particular universal identifier. Remote server system 102 may request access to Internet accessible server system 84 in order to access electronic recipes 86 for searching electronic recipes 86 and/or downloading electronic recipes 86.

Moreover, universally accessible database 97 directs access to a remote server system 106 that comprises dietary and health data for a particular user stored according to a particular universal identifier. Remote server system 102 may request access to remote server system 106 for accessing dietary and health data for a particular user.

By remotely accessing eCookbooks data 98, a user may access a personal electronic cookbook from any computer system with access to a network including universally accessible database 97. In addition, by remotely processing eCookbooks data 98, a user may select a remote server system with a fast processing speed in relation to the processing speed of computer system 10, such that a user may utilize a computer system with limited processing power to access designated menu selections. Moreover, if computer system 10 is provided at a venue, such as a grocery store, the grocery store does not provide the user with processing power for determining designated menu selections, however it does provide an interface for accessing an electronic cookbook that determines designated menu selections at a remote system.

Figure 5:
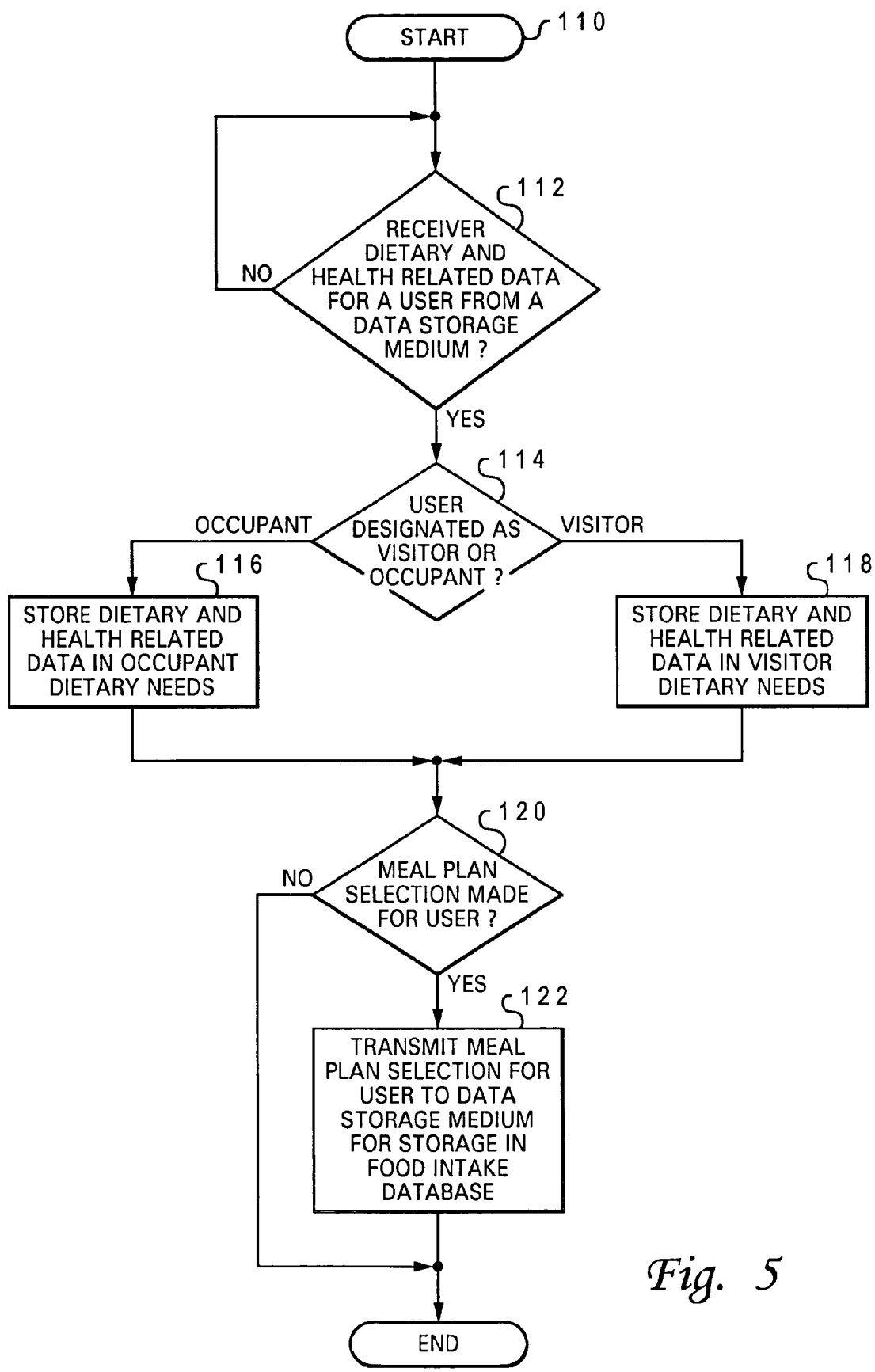
FIG. 5 illustrates a high level logic flowchart of a process and program for receiving dietary and health related data for a particular user at an electronic cookbook in accordance with the present invention.

With reference now to FIG. 5, there is depicted a high level logic flowchart of a process and program for receiving dietary and health related data for a particular user at an electronic cookbook in accordance with the present invention. As illustrated, the process starts at block 110 and thereafter proceeds to block 112. Block 112 depicts a determination as to whether or not dietary and health related data is received for a user from a data storage medium at an electronic cookbook. If dietary and health related data is not received, then the process iterates at block 112. If dietary and health related data is received, then the process passes to block 114. Block 114 depicts a determination as to whether or not the user is designated as a visitor or occupant. A list of occupants may be included on the electronic cookbook or the primary chef may designate whether the user is an occupant or visitor. If the user is an occupant, then the dietary and health related data is stored in the occupant dietary needs of the computer system as depicted at block 116; and the process passes to block 120. If the user is a visitor, then the dietary and health related data is stored in the visitor dietary needs of the computer system as illustrated at block 118; and the process passes to block 126.

Block 120 illustrates a determination as to whether or not a meal plan selection is made for the user by the electronic cookbook. If a meal plan selection for the user is not made, then the process ends. If a meal plan selection for the user is made, then the process passes to block 122. Block 122 depicts transmitting the meal plan selection for the user from the electronic cookbook to the data storage medium associated with the user for storage in a food intake database included on the data storage medium; and the process ends.

Figure 6:
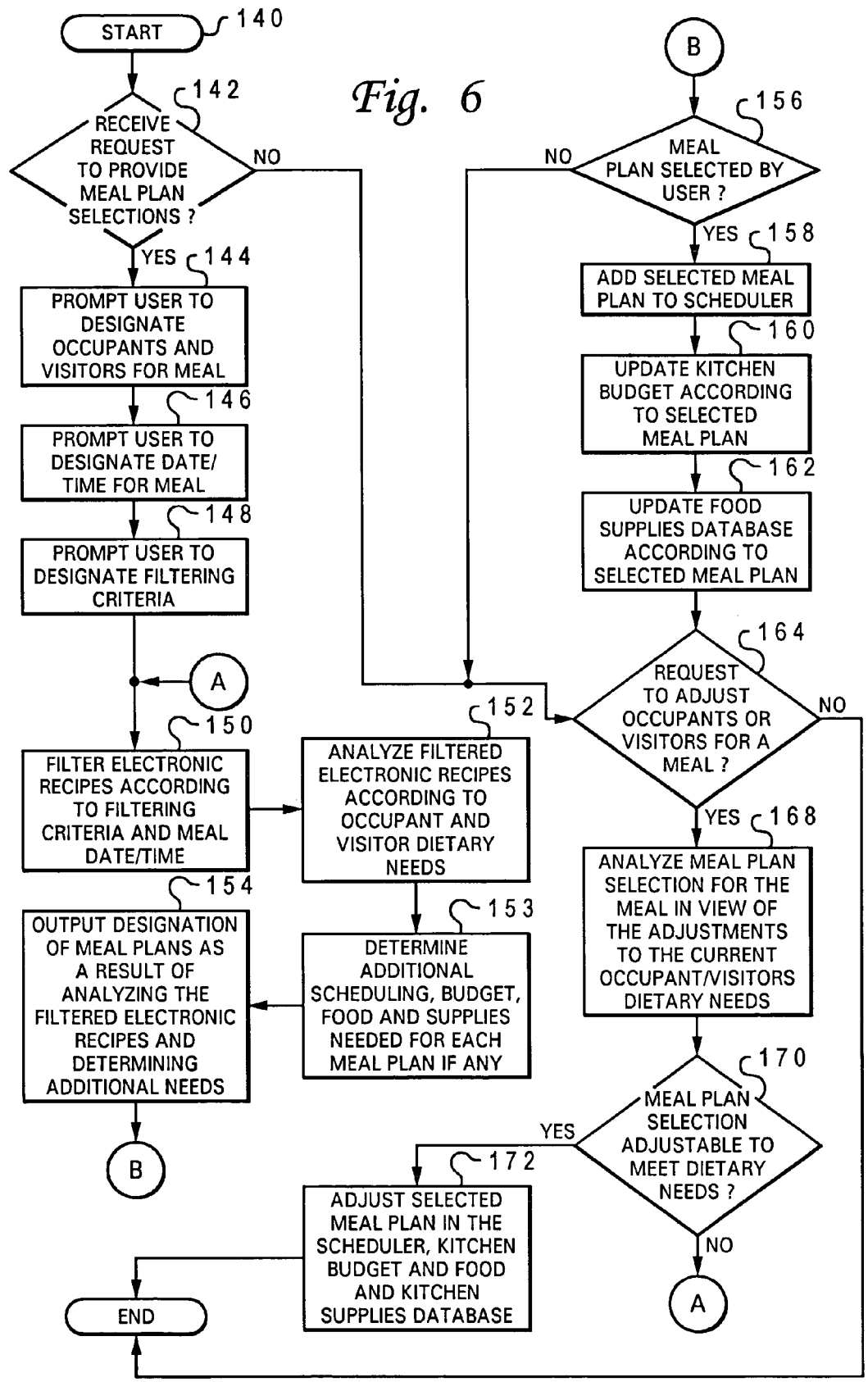
FIG. 6 depicts a high level logic flowchart of a process and program for managing an electronic cookbook to provide a selection of meal plans in accordance with the present invention.

Referring now to FIG. 6, there is illustrated a high level logic flowchart of a process and program for managing an electronic cookbook to provide a selection of meal plans in accordance with the present invention. As depicted, the process starts at block 140 and thereafter proceeds to block 142. Block 142 illustrates a determination as to whether or not a request is received to provide meal plan selections. If not a request to provide meal plan selections is not received, then the process passes to block 164. If a request to provide meal plan selections is received, then the process passes to block 144. Block 144 depicts prompting a user to designate occupants and visitor for a meal. Next, block 146 illustrates prompting a user to designate the date/time for a meal. Thereafter, block 148 depicts prompting a user to designate filtering criteria. Filtering criteria may include utilizing the kitchen supplies database, food supplies database, scheduler, kitchen budget and/or additional data accessed from alternate data servers such as regional weather forecasts. Next, block 150 illustrates filtering the electronic recipes according to the filtering criteria and meal date/time. In addition, when filtering electronic recipes, ingredient substitutions may be made such that more recipes are available. Block 152 depicts analyzing the filtered electronic recipes according the designated occupant and visitor dietary needs. Next, block 153 illustrates a determination as to whether or not additional scheduling, budgeting, or food and kitchen supplies are needed for each of the meal plans, if any. Thereafter, block 154 illustrates outputting a designation of acceptable meal plans with any additional needs as a result of analyzing the filtered electronic recipes. The process next passes to block 156. If the electronic cookbook is located at a computer system, then the computer system controls output of the designation of acceptable meal plans to an output interface controlled by the computer system. If the electronic cookbook is located at a universally accessible server system, then the designation of acceptable meal plans is output to a computer system that controls an output interface.

Block 156 depicts a determination as to whether or not a particular meal plan is selected by a user, where the user is preferably the primary chef for the residence. If a meal plan is not selected, then the process passes to block 164. If a meal plan is selected, then the process passes to block 158. Block 158 illustrates adding the selected meal plan to the scheduler. Next, block 160 depicts updating the kitchen budget according the selected meal plan. Thereafter, block 162 illustrates updating the food supplies database according to the selected meal plan; and the process passes to block 164. Block 164 depicts a determination as to whether or not a request to adjust the occupants and visitors eating a selected meal is requested. If a request to adjust the occupants and visitors is not requested, then the process ends. If a request to adjust the occupants and visitors is requested, then the process passes to block 168. Block 168 illustrates analyzing the meal plan selection in view of the adjustment to the occupants and visitors. Block 170 depicts a determination as to whether or not the current meal plan can be adjusted to meet the dietary needs adjustment. If the current meal plan cannot be adjusted, then the process passes to block 150. If the current meal plan can be adjusted, then the process passes to block 172. Block 172 illustrates adjusting the current meal plan in the scheduler, kitchen budget and food supplies database; and the process ends.

Figure 7:
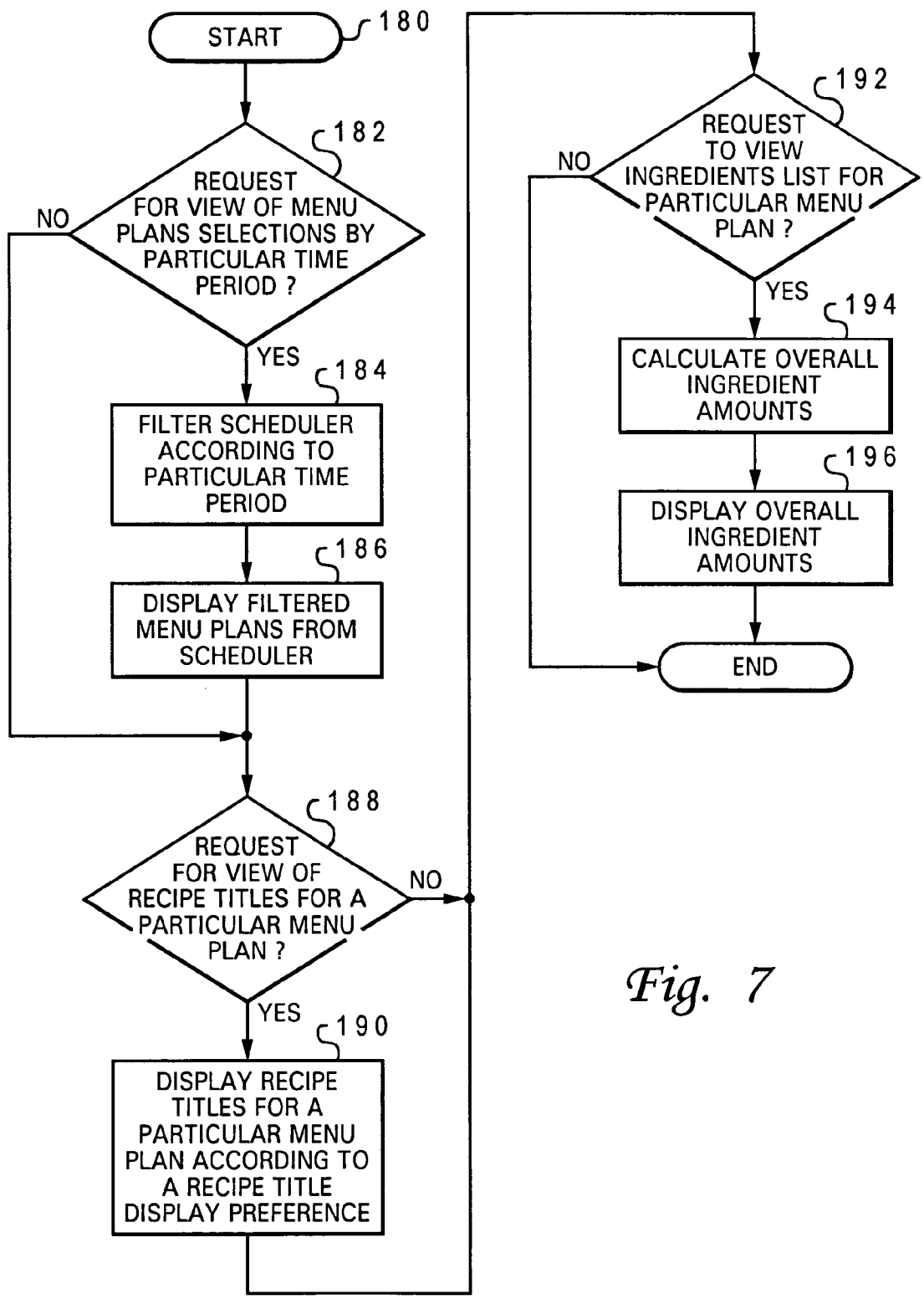
FIG. 7 illustrates a high level logic flowchart of a process and program for displaying menu plan selections on an electronic cookbook in accordance with the present invention.

With reference now to FIG. 7, there is depicted a high level logic flowchart of a process and program for displaying menu plan selections on an electronic cookbook in accordance with the present invention. As depicted, the process starts at block 180 and thereafter proceeds to block 182. Block 182 illustrates a determination as to whether or not a request for a view of the menu plan selections within a particular time period is received. For example, the menu plan selections for the next four days may be selected or the menu plan selections from the previous Thanksgiving day may be selected. If a request for a view of the menu plan selections within a particular time period is not received, then the process passes to block 188. If a request for a view of the menu plan selections with a particular time period is received, then the process passes to block 184. Block 184 depicts filtering the scheduler for menu plan selections according to the particular time period. Next, block 186 illustrates displaying the filtered menu plans from the scheduler; and the process passes to block 188.

Block 188 depicts a determination as to whether or not a request for a view of the recipe titles for a particular menu plan is received. If a request for a view of the recipe titles for a particular menu plan is not received, then the process passes to block 192. If a request for a view of the recipe titles for a particular menu plan is received, then the process passes to block 190. Block 190 illustrates displaying the recipe titles for a particular menu plan according to a recipe title display preference; and the process passes to block 192. Multiple display templates for displaying recipe titles for a meal plan are preferably included. For example, a display template that includes a Mexican fiesta theme may be provided for displaying recipe titles for a meal plan including Mexican food. The display of the recipe titles is further editable by the user and may be printed.

Block 192 illustrates a determination as to whether or not a request for a view of an ingredients list for a particular menu plan is received. If a request for a view of an ingredients list for a particular menu plan is not received, then the process ends. If a request for a view of an ingredients list for a particular menu plan is received, then the process passes to block 194. Block 194 depicts calculating the overall ingredient amounts for the meal plan. For example, a meal plan may include five recipes where three of the recipes call for olive oil. The total olive oil utilized in the three recipes would be calculated. Thereafter, block 196 illustrates displaying the overall ingredient amounts; and the process ends.

It is important to note that the process depicted in FIG. 7 is an example of a selection of views that may be requested by a user, however the views of meal plans and recipes is not intended to be limited according to the examples utilized. In addition, it is important to note that the user may customize display options and print output options according to the display and print quality of the output interfaces utilized.

It is important to note that, although the present invention has been described in the context of a fully functional computer system, those skilled in the art will appreciate that the mechanisms of the present invention are capable of being distributed as a program product in a variety of forms; and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

While the invention has been particularly shown and described with reference to a preferred embodiment, it will be understood by those skilled in the art that various changes in form and detail may be made therein without departing from the spirit and scope of the invention.

What is claimed is:

1. A method for managing an electronic cookbook, said method comprising the steps of:
   receiving dietary needs designated for a particular user in a particular transmittable data format at a data processing system associated with a particular home base, wherein said data processing system has access to a plurality of electronic recipes;
   comparing said dietary needs designated for said particular user with a selection of electronic recipes that are preparable at said particular home base from among said plurality of electronic recipes;
   designating at least one meal plan of recipes from among said selection of electronic recipes that satisfies said dietary needs for said particular user, such that an electronic meal plan is specified on said data processing system for preparation at said particular home base according to said dietary needs of said particular user; and
   in response to receiving a meal plan selection from among said at least one meal plan, updating a kitchen budget according to cost of cooking related supplies utilized for said meal plan selection.

2. The method for managing an electronic cookbook according to claim 1, said step of receiving dietary needs designated for a particular user in said transmittable data format further comprising the step of:
   receiving said dietary needs in an extensible mark-up language data format.

3. The method for managing an electronic cookbook according to claim 1, said step of receiving dietary needs designated for a particular user in said transmittable data format further comprising the step of:
   receiving said dietary needs from a portable data processing system associated with said particular user, wherein said plurality of dietary needs are stored at said portable data processing system.

4. The method for managing an electronic cookbook according to claim 1, said step of receiving dietary needs designated for a particular user in said transmittable data format further comprising the step of:
   receiving said dietary needs from a personal storage device proffered by said particular user at said data processing system.

5. The method for managing an electronic cookbook according to claim 1, said step of receiving dietary needs designated for a particular user in said transmittable data format further comprising the step of:

receiving said dietary needs from a universally accessible server system according to a particular universal identifier associated with said particular user.

6. The method for managing an electronic cookbook according to claim 1, said step of receiving dietary needs designated for a particular user in said transmittable data format further comprising the step of:

receiving a dietary health plan for said particular user in said dietary needs.

7. The method for managing an electronic cookbook according to claim 1, said step of receiving dietary needs designated for a particular user in said transmittable data format further comprising the step of:

receiving intake indicators for said particular user in said dietary needs, wherein said intake indicators include food, liquid and medication intake by said particular user within a particular time period.

8. The method for managing an electronic cookbook according to claim 1, said step of receiving dietary needs designated for a particular user in said transmittable data format further comprising the step of:

receiving exercise indicators for said particular user in said dietary needs, wherein said exercise indicators indicate fitness levels for said particular user within a particular time period.

9. The method for managing an electronic cookbook according to claim 1, said step of receiving dietary needs designated for a particular user in said transmittable data format further comprising the step of:

receiving environmental exposure indicators for said particular user in said dietary needs, wherein said environmental exposure indicators indicate recorded environmental exposure of said particular user within a particular period of time.

10. The method for managing an electronic cookbook according to claim 1, said step of receiving dietary needs designated for a particular user in a particular transmittable data format at a data processing system associated with a particular home base, wherein said data processing system has access to a plurality of electronic recipes, further comprising the step of:

accessing said plurality of electronic recipes from a network accessible server system comprising a plurality of electronic recipes.

11. The method for managing an electronic cookbook according to claim 1, said method further comprising the step of:

storing said dietary needs for said particular user at said data processing system in accordance with an user status of said particular user.

12. The method for managing an electronic cookbook according to claim 1, said method further comprising the step of:

controlling output of said at least one designated meal plan from said data processing system to an output interface according to user-designated output preferences.

13. The method for managing an electronic cookbook according to claim 1, said step of comparing said dietary needs designated for said particular user with a selection of electronic recipes that are preparable at said particular home base further comprising the step of:

comparing said dietary needs designated for said particular user with a user-designated selection of electronic recipes from among said plurality of electronic recipes.

14. The method for managing an electronic cookbook according to claim 1, said method further comprising the step of:

designating said selection of electronic recipes that are preparable at said particular home base according to ingredients that are currently available at said home base.

15. The method for managing an electronic cookbook according to claim 1, said method further comprising the step of:

designating said selection of electronic recipes that are preparable at said particular home base according to the lifetime of ingredients that are currently available at said home base.

16. The method for managing an electronic cookbook according to claim 1, said step of comparing said dietary needs designated for said particular user with a selection of electronic recipes that are preparable at said particular home base further comprising the step of:

designating said selection of electronic recipes that are preparable at said particular home base according to estimated preparation and cooking times that satisfy designated meal preparation time constraints.

17. The method for managing an electronic cookbook according to claim 1, said step of comparing said dietary needs designated for said particular user with a selection of electronic recipes that are preparable at said particular home base further comprising the step of:

designating said selection of electronic recipes that are preparable at said particular home base according to preselected food preferences for said home base.

18. The method for managing an electronic cookbook according to claim 1, said step of comparing said dietary needs designated for said particular user with a selection of electronic recipes that are preparable at said particular home base further comprising the step of:

designating said selection of electronic recipes that are preparable at said particular home base according to a designated event.

19. The method for managing an electronic cookbook according to claim 1, said step of comparing said dietary needs designated for said particular user with a selection of electronic recipes that are preparable at said particular home base further comprising the step of:

designating said selection of electronic recipes that are preparable at said particular home base according to a food budget for said particular home base.

20. The method for managing an electronic cookbook according to claim 1, said step of comparing said dietary needs designated for said particular user with a selection of electronic recipes that are preparable at said particular home base Her comprising the step of:

comparing said dietary needs designated for said particular user and dietary needs for additional users with said selection of electronic recipes that are preparable at said particular home base.

21. The method for managing an electronic cookbook according to claim 1, said step of comparing said dietary needs designated for said particular user with a selection of electronic recipes that are preparable at said particular home base further comprising the step of:

adjusting a plurality of accessible electronic recipes to utilize ingredients currently available at said home base.

22. The method for managing an electronic cookbook according to claim 1, said step of comparing said dietary needs designated for said particular user with a selection of electronic recipes that are preparable at said particular home base further comprising the step of:

adjusting said selection of electronic recipes to substitute ingredients indicated in said dietary needs to be eliminated with alternative ingredients.

23. The method for managing an electronic cookbook according to claim 1, said step of receiving said dietary needs designated for said particular user further comprising the step of:

receiving current medication usage for said particular user in said transmittable data format at said data processing system.

24. The method for managing an electronic cookbook according to claim 23, said method further comprising the steps of:

comparing ingredients utilized in said at least one designated weal plan and medication usage for said particular user with medication summaries for said current medication usage; and alerting said particular user of any food and medication conflicts between said at least one designated meal plan and said medication usage.

25. The method for managing an electronic cookbook according to claim 1, said method further comprising the steps of:

receiving a plurality of cooking related purchases for said particular home base at said data processing system; and storing said plurality of cooking related purchases in a database of available cooking related items at said particular home base.

26. The method for managing an electronic cookbook according to claim 1, said method further comprising the step of:

recommending additional cooking related purchases to supplement currently available ingredients and equipment.

27. The method for managing an electronic cookbook according to claim 1, said method further comprising the step of:

in response to receiving a meal plan selection from among said at least one meal plan, updating a data storage medium storing said dietary needs for said particular user with said meal plan selection.

28. A method for managing an electronic cookbook, said method comprising the steps of:

receiving dietary needs designated for a particular user in a particular transmittable data format at a data processing system associated with a particular home base, wherein said data processing system has access to a plurality of electronic recipes;

comparing said dietary needs designated for said particular user with a selection of electronic recipes that are preparable at said particular home base from among said plurality of electronic recipes;

designating at least one meal plan of recipes from among said selection of electronic recipes that satisfies said dietary needs for said particular user, such that an electronic meal plan is specified on said data processing system for preparation at said particular home base according to said dietary needs of said particular user; and designating said selection of electronic recipes that are preparable at said particular home base according to kitchen equipment necessary to prepare said electronic recipes available at said home base.

29. A method for managing an electronic cookbook, said method comprising the steps of:

receiving dietary needs designated for a particular user in a particular transmittable data format at a data processing system associated with a particular home base, wherein said data processing system has access to a plurality of electronic recipes;

comparing said dietary needs designated for said particular user with a selection of electronic recipes that are preparable at said particular home base from among said plurality of electronic recipes;

designating at least one meal plan of recipes from among said selection of electronic recipes that satisfies said dietary needs for said particular users such that an electronic meal plan is specified on said data processing system for preparation at said particular home base according to said dietary needs of said particular user; and adding events to a schedule according to a meal plan selection, in response to receiving a meal plan selection from among said at least one meal plan.

30. The method for managing an electronic cookbook according to claim 29, said method further comprising the step of:

adding events to a schedule for purchasing cooking related supplies for preparing said meal plan selection.

31. The method for managing an electronic cookbook according to claim 29, said method further comprising the step of:

adding events to a schedule for preparation and cooking time for said particular meal plan selection.

32. A system for managing an electronic cookbook, said system comprising:

means for receiving dietary needs designated for a particular user in a particular transmittable data format at a data processing system associated with a particular home base, wherein said data processing system has access to a plurality of electronic recipes;

means for comparing said dietary needs designated for said particular user with a selection of electronic recipes that are preparable at said particular home base from among said plurality of electronic recipes; and means for designating at least one meal plan from among said selection of electronic recipes that satisfies said dietary needs for said particular user, such that an electronic meal plan is specified on said data processing system for preparation at said particular home base according to said dietary needs of said particular user;

means for, in response to receiving a meal plan selection from among said at least one meal plan, updating a kitchen budget according to cost of cooking related supplies utilized for said meal plan selection.

33. The system for managing an electronic cookbook according to claim 32, said means for receiving dietary needs designated for a particular user in said transmittable data format further comprising:

means for receiving said dietary needs in an extensible mark-up language data format.

34. The system for managing an electronic cookbook according to claim 32, said means for receiving dietary needs designated for a particular user in said transmittable data format further comprising:

means for receiving said dietary needs from a portable data processing system associated with said particular user, wherein said plurality of dietary needs are stored at said portable data processing system.

35. The system for managing an electronic cookbook according to claim 32, said means for receiving dietary needs designated for a particular user in said transmittable data format further comprising:
  means for receiving said dietary needs from a personal storage device proffered by said particular user at said data processing system.

36. The system for managing an electronic cookbook according to claim 32, said means for receiving dietary needs designated for a particular user in said transmittable data format further comprising:
  means for receiving said dietary needs from a universally accessible server system according to a particular universal identifier associated with said particular user.

37. The system for managing an electronic cookbook according to claim 32, said means for receiving dietary needs designated for a particular user in said transmittable data format further comprising:
  means for receiving a dietary health plan for said particular user in said dietary needs.

38. The system for managing an electronic cookbook according to claim 32, said means for receiving dietary needs designated for a particular user in said transmittable data format further comprising:
  means for receiving intake indicators for said particular user in said dietary needs, wherein said intake indicators include food, liquid and medication intake by said particular user within a particular time period.

39. The system for managing an electronic cookbook according to claim 32, said means for receiving dietary needs designated for a particular user in said transmittable data format further comprising:
  means for receiving exercise indicators for said particular user in said dietary needs, wherein said exercise indicators indicate fitness levels for said particular user within a particular time period.

40. The system for managing an electronic cookbook according to claim 32, said means for receiving dietary needs designated for a particular user in said transmittable data format further comprising:
  means for receiving environmental exposure indicators for said particular user in said dietary needs, wherein said environmental exposure indicators indicate recorded environmental exposure of said particular user within a particular period of time.

41. The system for managing an electronic cookbook according to claim 32, said means for receiving dietary needs designated for a particular user in a particular transmittable data format at a data processing system associated with a particular home base, wherein said data processing system has access to a plurality of electronic recipes, further comprising:
  means for accessing said plurality of electronic recipes from a network accessible server system comprising a plurality of electronic recipes.

42. The system for managing an electronic cookbook according to claim 32, said system further comprising:
  means for storing said dietary needs for said particular user at said data processing system in accordance with an user status of said particular user.

43. The system for managing an electronic cookbook according to claim 32, said system further comprising:
  means for controlling output of said at least one designated meal plan from said data processing system to an output interface according to user-designated output preferences.

44. The system for managing an electronic cookbook according to claim 32, said means for comparing said dietary needs designated for said particular user with a selection of electronic recipes that are preparable at said particular home base further comprising:
  means for comparing said dietary needs designated for said particular user with a user-designated selection of electronic recipes from among said plurality of electronic recipes.

45. The system for managing an electronic cookbook according to claim 32, said means for comparing said dietary needs designated for said particular user with a selection of electronic recipes that are preparable at said particular home base further comprising:
  means for designating said selection of electronic recipes that are preparable at said particular home base according to ingredients that are currently available at said home base.

46. The system for managing an electronic cookbook according to claim 32, said means for comparing said dietary needs designated for said particular user with a selection of electronic recipes that are preparable at said particular home base further comprising:
  means for designating said selection of electronic recipes that are preparable at said particular home base according to the lifetime of ingredients that are currently available at said home base.

47. The system for managing an electronic cookbook according to claim 32, said means for comparing said dietary needs designated for said particular user with a selection of electronic recipes that are preparable at said particular home base further comprising:
  means for designating said selection of electronic recipes that are preparable at said particular home base according to estimated preparation and cooking times that satisfy designated meal preparation time constraints.

48. The system for managing an electronic cookbook according to claim 32, said means for comparing said dietary needs designated for said particular user with a selection of electronic recipes that are preparable at said particular home base further comprising:
  means for designating said selection of electronic recipes that are preparable at said particular home base according to preselected food preferences for said home base.

49. The system for managing an electronic cookbook according to claim 32, said means for comparing said dietary needs designated for said particular user with a selection of electronic recipes that are preparable at said particular home base further comprising:
  means for designating said selection of electronic recipes that are preparable at said particular home base according to a designated event.

50. The system for managing an electronic cookbook according to claim 32, said means for comparing said dietary needs designated for said particular user with a selection of electronic recipes that are preparable at said particular home base further comprising:
  means for designating said selection of electronic recipes that are preparable at said particular home base according to a food budget for said particular home base.

51. The system for managing an electronic cookbook according to claim 32, said means for comparing said dietary needs designated for said particular user with a selection of electronic recipes that are preparable at said particular home base further comprising:
  means for comparing said dietary needs designated for said particular user and dietary needs for additional users with said selection of electronic recipes that are preparable at said particular home base.

52. The system for managing an electronic cookbook according to claim 32, said means for comparing said dietary needs designated for said particular user with a selection of electronic recipes that are preparable at said particular home base further comprising:

means for adjusting a plurality of accessible electronic recipes to utilize ingredients currently available at said home base.

53. The system for managing an electronic cookbook according to claim 32, said means for comparing said dietary needs designated for said particular user with a selection of electronic recipes that are preparable at said particular home base further comprising:

means for adjusting said selection of electronic recipes to substitute ingredients indicated in said dietary needs to be eliminated with alternative ingredients.

54. The system for managing an electronic cookbook according to claim 32, said means for receiving said dietary needs designated for said particular user further comprising:

means for receiving current medication usage for said particular user in said transmittable data format at said data processing system.

55. The system for managing an electronic cookbook according to claim 54, said system further:

means for comparing ingredients utilized in said at least one designated meal plan and medication usage for said particular user with medication summaries for said current medication usage; and means for alerting said particular user of any food and medication conflicts between said at least one designated meal plan and said medication usage.

56. The system for managing an electronic cookbook according to claim 32, said system further comprising:

means for receiving a plurality of cooking related purchases for said particular home base at said data processing system; and means for storing said plurality of cooking related purchases in a database of available cooking related items at said particular home base.

57. The system for managing an electronic cookbook according to claim 32, said system further comprising:

means for recommending additional cooking related purchases to supplement currently available ingredients and equipment.

58. The system for managing an electronic cookbook according to claim 32, said system further comprising:

means for in response to receiving a meal plan selection from among said at least one meal plan, updating a data storage medium storing said dietary needs for said particular user with said meal plan selection.

59. A system for managing an electronic cookbook, said system comprising:

means for receiving dietary needs designated for a particular user in a particular transmittable data format at a data processing system associated with a particular home base, wherein said data processing system has access to a plurality of electronic recipes;

means for comparing said dietary needs designated for said particular user with a selection of electronic recipes that are preparable at said particular home base from among said plurality of electronic recipes;

means for designating at least one meal plan from among said selection of electronic recipes that satisfies said dietary needs for said particular user, such that an electronic meat plan is specified on said data processing system for preparation at said particular home base according to said dietary needs of said particular user; and means for designating said selection of electronic recipes that are preparable at said particular home base according to kitchen equipment necessary to prepare said electronic recipes available at said home base.

60. A system for managing an electronic cookbook, said system comprising:

means for receiving dietary needs designated for a particular user in a particular transmittable data format at a data processing system associated with a particular home base wherein said data processing system has access to a plurality of electronic recipes;

means for comparing said dietary needs designated for said particular user with a selection of electronic recipes that are preparable at said particular home base from among said plurality of electronic recipes; and means for designating at least one meal plan from among said selection of electronic recipes that satisfies said dietary needs for said particular user, such that an electronic meal plan is specified on said data processing system for preparation at said particular home base according to said dietary needs of said particular user;

means for adding events to a schedule according to a meal plan selection, in response to receiving a meal plan selection from among said at least one meal plan.

61. The system for managing an electronic cookbook according to claim 60, said system further comprising:

means for adding events to a schedule for purchasing cooking related supplies for preparing said meal plan selection.

62. The system for managing an electronic cookbook according to claim 60, said system further comprising:

means for adding events to a schedule for preparation and cooking time for said particular meal plan selection.

63. A program for managing an electronic cookbook, residing on a computer usable medium having computer readable program code means, said program comprising:

means for receiving dietary needs designated for a particular user in a particular transmittable data format at a data processing system associated with a particular home base, wherein said data processing system has access to a plurality of electronic recipes;

means for comparing said dietary needs designated for said particular user with a selection of electronic recipes that are preparable at said particular home base from among said plurality of electronic recipes;

means for designating at least one meal plan from among said selection of electronic recipes that satisfies said dietary needs for said particular user, such that an electronic meal plan is specified on said data processing system for preparation at said particular home base according to said dietary needs of said particular user; and means for, in response to receiving a meal plan selection from among said at least one meal plan, updating a kitchen budget according to cost of cooking related supplies utilized for said meal plan selection.

64. The program for managing an electronic cookbook according to claim 63, said program further comprising:

means for receiving said dietary needs in an extensible mark-up language data format.

65. The program for managing an electronic cookbook according to claim 63, said program further comprising:

means for accessing said plurality of electronic recipes from a network accessible server system comprising a plurality of electronic recipes.

66. The program for managing an electronic cookbook according to claim 63, said program further comprising:
means for storing said dietary needs for said particular user at said data processing system in accordance with an user status of said particular user.

67. The program for managing an electronic cookbook according to claim 63, said program further comprising:
means for controlling output of said at least one designated meal plan from said data processing system to an output interface according to user-designated output preferences.

68. The program for managing an electronic cookbook according to claim 63, said program further comprising:
means for comparing said dietary needs designated for said particular user with a user-designated selection of electronic recipes from among said plurality of electronic recipes.

69. The program for managing an electronic cookbook according to claim 63, said program further comprising:
means for designating said selection of electronic recipes that are preparable at said particular home base according to ingredients that are currently available at said home base.

70. The program for managing an electronic cookbook according to claim 63, said program further comprising:
means for designating said selection of electronic recipes that are preparable at said particular home base according to the lifetime of ingredients that are currently available at said home base.

71. The program for managing an electronic cookbook according to claim 63, said program further comprising:
means for designating said selection of electronic recipes that are preparable at said particular home base according to estimated preparation and cooking times that satisfy designated meal preparation time constraints.

72. The program for managing an electronic cookbook according to claim 63, said program further comprising:
means for designating said selection of electronic recipes that are preparable at said particular home base according to preselected food preferences for said home base.

73. The program for managing an electronic cookbook according to claim 63, said program further comprising:
means for designating said selection of electronic recipes that are preparable at said particular home base according to a designated event.

74. The program for managing an electronic cookbook according to claim 63, said program further comprising:
means for designating said selection of electronic recipes that are preparable at said particular home base according to a food budget for said particular home base.

75. The program for managing an electronic cookbook according to claim 63, said program further comprising:
means for comparing said dietary needs designated for said particular user and dietary needs for additional users with said selection of electronic recipes that are preparable at said particular home base.

76. The program for managing an electronic cookbook according to claim 63, said program further comprising:
means for adjusting a plurality of accessible electronic recipes to utilize ingredients currently available at said home base.

77. The program for managing an electronic cookbook according to claim 63, said program further comprising:
means for adjusting said selection of electronic recipes to substitute ingredients indicated in said dietary needs to be eliminated with alternative ingredients.

78. The program for managing an electronic cookbook according to claim 63, said program further comprising:
means for receiving current medication usage for said particular user in said transmittable data format at said data processing system.

79. The program for managing an electronic cookbook according to claim 63, said program further:
means for comparing ingredients utilized in said at least one designated meal plan and medication usage for said particular user with medication summaries for said current medication usage; and
means for alerting said particular user of any food and medication conflicts between said at least one designated meal plan and said medication usage.

80. The program for managing an electronic cookbook according to claim 63, said program further comprising:
means for receiving a plurality of cooking related purchases for said particular home base at said data processing system; and
means for storing said plurality of cooking related purchases in a database of available cooking related items at said particular home base.

81. The program for managing an electronic cookbook according to claim 63, said program further comprising:
means for recommending additional cooking related purchases to supplement currently available ingredients and equipment.

82. A program for managing an electronic cookbook, residing on a computer usable medium having computer readable program code means, said program comprising:
means for receiving dietary needs designated for a particular user in a particular transmittable data format at a data processing system associated with a particular home base, wherein said data processing system has access to a plurality of electronic recipes;
means for comparing said dietary needs designated for said particular user with a selection of electronic recipes that are preparable at said particular home base from among said plurality of electronic recipes;
means for designating at least one meal plan from among said selection of electronic recipes that satisfies said dietary needs for said particular user, such that an electronic meal plan is specified on said data processing system for preparation at said particular home base according to said dietary needs of said particular user; and
means for designating said selection of electronic recipes that are preparable at said particular home base according to kitchen equipment necessary to prepare said electronic recipes available at said home base.

83. A program for managing an electronic cookbook, residing on a computer usable medium having computer readable program code means, said program comprising:
means for receiving dietary needs designated for a particular user in a particular transmittable data format at a data processing system associated with a particular home base, wherein said data processing system has access to a plurality of electronic recipes;
means for comparing said dietary needs designated for said particular user with a selection of electronic recipes that are preparable at said particular home base from among said plurality of electronic recipes;
means for designating at least one meal plan from among said selection of electronic recipes that satisfies said dietary needs for said particular user, such that an electronic meal plan is specified on said data processing system for preparation at said particular home base according to said dietary needs of said particular user; and means for adding events to a schedule according to a meal plan selection, in response to receiving a meal plan selection from among said at least one meal plan.

84. The program for managing an electronic cookbook according to claim 83, said program further comprising:
   means for adding events to a schedule for purchasing cooking related supplies for preparing said meal plan selection.

85. The program for managing an electronic cookbook according to claim 83, said program further comprising:
   means for adding events to a schedule for preparation and cooking time for said particular meal plan selection.

86. A method for managing recipe selections within an electronic cookbook, said method comprising the steps of:
   receiving access to a plurality of electronic recipes via a plurality of diverse data storage medium at an electronic cookbook controller; and
   filtering said plurality of electronic recipes at said electronic cookbook controller according to specifications for a particular household and according to kitchen equipment accessible at said particular household, such that only a selection of said plurality of electronic recipes that are preparable according to said specifications for said particular household and said kitchen equipment accessible at said particular household are accessible at said electronic cookbook controller.

87. The method for managing recipe selections within an electronic cookbook according to claim 86, said step of receiving access to a plurality of electronic recipes via a plurality of diverse data storage medium, further comprising the step of:
   accessing said plurality of electronic recipes via a network connection to a plurality of servers each comprising electronic recipes.

88. The method for managing recipe selections within an electronic cookbook according to claim 86, said step of filtering said plurality of electronic recipes at said electronic recipe controller according to specifications for a particular household, further comprising the step of:
   filtering said plurality of electronic recipes according to available preparation and cooking times scheduled for said particular household.

89. The method for managing recipe selections within an electronic cookbook according to claim 86, said step of filtering said plurality of electronic recipes at said electronic recipe controller according to specifications for a particular household, further comprising the step of:
   filtering said plurality of electronic recipes according to a designated food-related event scheduled for said particular household.

90. The method for managing recipe selections within an electronic cookbook according to claim 86, said method further comprising the step of:
   determining additional cooking related purchases to supplement currently available ingredients and equipment at said electronic cookbook controller.

91. A method for managing recipe selections within an electronic cookbook, said method comprising the steps of:
   receiving access to a plurality of electronic recipes via a plurality of diverse data storage medium at an electronic cookbook controller;
   filtering said plurality of electronic recipes at said electronic cookbook controller according to specifications for a particular household, such that only a selection of said plurality of electronic recipes that are preparable according to said specifications for said particular household are accessible at said electronic cookbook controller, and further according to kitchen equipment accessible at said particular household;
   filtering said plurality of electronic recipes at said electronic cookbook controller according to specifications for a particular household, such that only a selection of said plurality of electronic recipes that at preparable according to said specifications for said particular household are accessible at said electronic cookbook controller; and
   adding events to a schedule according to a selection from among said filtered plurality of recipes.

\* \* \* \* \*